US009599586B2

(12) United States Patent
Krivec et al.

(10) Patent No.: US 9,599,586 B2
(45) Date of Patent: Mar. 21, 2017

(54) ION SENSOR

(75) Inventors: Stefan Krivec, Villach (AT); Guenter Schagerl, Finkenstein (AT)

(73) Assignee: Infineon Technologies AG, Neubiberg (DE)

( * ) Notice: Subject to any disclaimer, the term of this patent is extended or adjusted under 35 U.S.C. 154(b) by 534 days.

(21) Appl. No.: 13/595,019

(22) Filed: Aug. 27, 2012

(65) Prior Publication Data

US 2014/0055145 A1    Feb. 27, 2014

(51) Int. Cl.
*G01N 27/62*    (2006.01)
*G01N 27/414*    (2006.01)

(52) U.S. Cl.
CPC ........... *G01N 27/414* (2013.01); *G01N 27/62* (2013.01)

(58) Field of Classification Search
USPC ...... 324/459, 464, 465, 467, 468, 469, 71.1, 324/71.4, 762.09, 760; 257/253, 316, 257/414, E29.255, E21.409, E21.531; 204/411, 412, 419; 438/49
See application file for complete search history.

(56) References Cited

U.S. PATENT DOCUMENTS

| | | | |
|---|---|---|---|
| 4,716,448 A * | 12/1987 | Kelly ................ | G01N 27/4148 204/406 |
| 4,773,970 A * | 9/1988 | Purbrick ............ | G01N 27/3335 204/418 |
| 5,394,101 A | 2/1995 | Mitros | |
| 5,773,989 A | 6/1998 | Edelman et al. | |
| 5,790,463 A | 8/1998 | Gilliam | |
| 7,544,979 B2 * | 6/2009 | Morgenshtein et al. | ...... 257/253 |
| 7,799,205 B2 * | 9/2010 | Morgenshtein .... | G01N 27/4148 205/787.5 |
| 7,888,015 B2 * | 2/2011 | Toumazou ........... | C12Q 1/6825 435/6.11 |
| 2004/0178427 A1 * | 9/2004 | Chou ................... | G01N 27/414 257/253 |
| 2005/0062093 A1 * | 3/2005 | Sawada .............. | G01N 27/4145 257/316 |
| 2007/0235760 A1 * | 10/2007 | Shim et al. .................. | 257/192 |
| 2007/0252176 A1 * | 11/2007 | Shim .................. | G01N 27/4145 257/213 |
| 2008/0134759 A1 * | 6/2008 | Mohammed-Brahim et al. ............................ | 73/31.06 |
| 2008/0231253 A1 * | 9/2008 | Sawada .............. | G01N 27/4148 324/71.1 |
| 2008/0265985 A1 * | 10/2008 | Toumazou et al. .......... | 327/566 |

(Continued)

OTHER PUBLICATIONS

Grove et al., "Simple Physical Model for the Space-Charge Capacitance of Metal-Oxide-Semiconductor Structures", Journal of Applied Physics, vol. 35, No. 8, pp. 2458-2460, United States, Aug. 1964.

(Continued)

*Primary Examiner* — Jermele M Hollington
*Assistant Examiner* — Thang Le
(74) *Attorney, Agent, or Firm* — Murphy, Bilak & Homiller, PLLC (57) ABSTRACT

The disclosure describes techniques for determining an ion concentration in a sample. According to these techniques of this disclosure, an ion concentration of a sample is determined based on detecting at least one change in an electrical characteristic of a semiconductor device due to a gate insulation layer of the semiconductor device placed in contact with the sample.

16 Claims, 5 Drawing Sheets

(56) References Cited

U.S. PATENT DOCUMENTS

2010/0007326 A1* 1/2010 Nakazato ........... G01N 27/4148
                                                    324/71.5
2011/0100810 A1* 5/2011 Merz ............................. 204/406
2011/0210016 A1* 9/2011 Merz ............................. 205/789
2012/0001646 A1* 1/2012 Bolander et al. ............. 324/679

OTHER PUBLICATIONS

Dreizner et al., "A New Wafer Level Reliability Method for Evaluation of Ionic Induced PMOSFET Drift Effects", Microelectron. Reliab., vol. 36, No. 11/12, pp. 1855-1858, Enschede, The Netherlands, Oct. 8, 1996.

Stefan Krivec, Dissertation, "Investigations of mobile ion transport processes in thin layers upon bias-temperature stress", submitted to Technischen Universitaet Wien, May 16, 2011, pp. 1-147.

* cited by examiner

ION SENSOR

BACKGROUND AND RELATED ART

Field of the Invention

The present disclosure relates to a semiconductor sensor and to a method using such a semiconductor sensor for detecting mobile ions in a sample.

Background and Related Art

Measuring the quantitative concentration of mobile ions in liquid sample may be accomplished by chromatographic or spectroscopic methods as for instance HPLC (High-performance or high pressure liquid chromatography), GC-MS (Gas chromatography-mass spectrometry), AAS (Atomic absorption spectroscopy) or ICP-MS (Inductively coupled plasma mass spectrometry). Each approach has advantages in terms of ease of use and sensitivity, enabling the measurement of mobile ion down to a magnitude of ppm or even lower. These methods require large and expensive apparatus and specially trained personal.

In the health care industry testing of human blood samples is often performed. As one example, a blood sample may be tested for the presence of K+ (potassium ions), which may be performed using one or more of the above-described techniques. Such techniques may require a relatively long amount of time and/or substantial cost to perform.

At least some of the disadvantages of prior art can be overcome by the present invention.

SUMMARY OF THE INVENTION

The disclosure proposes an apparatus and a method for determining an ion concentration in a sample.

The apparatus comprises a semiconductor body, a gate electrode and a gate insulation arranged between the gate electrode and at least a portion of the semiconductor body. The gate insulation comprises at least one ion access area providing access for ions in the sample to the insulating layer.

The method comprises providing a sample on a sample access area of a gate insulation of a semiconductor field effect device structure, determining a change in an electric characteristic of the field effect device structure, and determining the ion concentration based on the change in the electric characteristic.

DETAILED DESCRIPTION

The invention may be better understood when reading the following detailed description of examples which are given with respect to the accompanying figures. The invention, however, is not limited to specific embodiments. Features described with respect to one example can be used and combined with features of a different example without departing from the scope of the present invention.

Like reference numerals are used to refer to like elements throughout. In the following description, for purposes of explanation, numerous specific details are set forth in order to provide a thorough understanding of the claimed subject matter. It may be evident, however, that the claimed subject matter may be practiced without these specific details. A repetitive description of features has been avoided and the figures may not be to scale relative to each other.

The disclosure describes a method and an apparatus for detecting ions and for determining an ion concentration in a sample using a semiconductor device. The semiconductor may thus be termed a semiconductor ion sensor.

Figure 1:
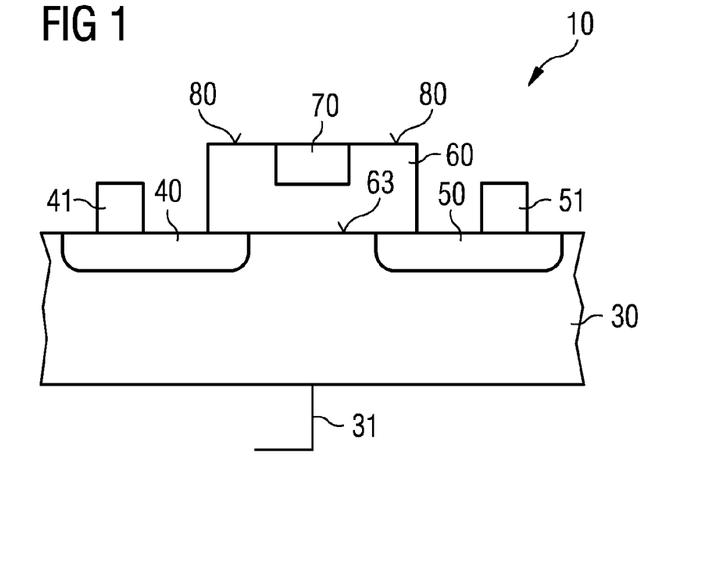
FIG. 1 shows an example of a field effect transistor structure for detection ions in a sample.

FIG. 1 shows an example of a field effect semiconductor device 10 for detecting ions. The field effect semiconductor device 10 may also be considered a detection module. The field effect semiconductor device 10 may have the structure of a field effect transistor comprising a source region 40 with a source contact 41, a drain region 50 with drain contact 51 and a body region 30 arranged between the source region 40 and the drain region 50. The body region 30 may have a body contact 31. The source region 40, the drain region 50 and the body region 30 may be made from silicon (Si) or any other semiconductor material that can be used for a field effect transistor. The source region 40 and the drain region 50 may be of a first conductivity type, and the body region 30 may be of a second conductivity type. The first conductivity type can be n-type and the second conductivity type can be p-type or the other way around. The field effect transistor structure 10 further comprises a gate electrode 70 and a gate insulation or gate insulation layer 60 separating the body region, the source region and the drain region from the gate electrode. The gate electrode 70 may be a polycrystaline silicon and the gate insulation 60 may be a gate oxide made from silicon dioxide (SiO2). This field effect transistor structure may correspond to a conventional field effect transistor or may be adapted for the use as an ion sensor. For example, according to the techniques described herein, the shape and the dimensions of the gate oxide 60 and/or of the gate electrode 70 or the gate-drain capacity may be adapted to the use of the field effect transistor structure as an ion sensor.

In conventional field effect transistors (FETs), the gate oxide is protected from the environment by one or more protective layers to protect the oxide from ions moving from the environment into the gate oxide. Ions in the gate oxide may alter the performance and in particular the transfer characteristics of the FET which usually is an unwanted effect in a FET. The transfer characteristics relate to the electrical properties of the transistor device and may comprise a relation between a drain current $I_D$ and an applied gate source voltage $V_{GS}$.

In some examples, a conventional FET is additionally processed to protect against any transmission of mobile ions into the gate isolation. For example, one or more of Imide, Silicon nitride, (boron) phosphorous silicate glass, one or more metal layers, substantially sealed packaging and/or any other structure may be added to a gate insulation to protect the gate insulation form ions. In some examples, the aforementioned techniques may be used in any combination to protect the gate insulation from ion transmission.

The present disclosure describes a field effect structure with at least one ion access area 80 providing access for mobile ion to the gate insulation 60. In one example, the ion access area 80 may be an area arranged to enable a sample 90 (shown in FIG. 3a) to come into substantially direct contact with the gate insulation 60. In some examples, no protective layer or ion barrier may be used. In other examples, the ion access area 80 may comprise a protective layer that is permeable at least ions which are to be detected. For example, a protective layer that is permeable to potassium ions may be used while larger or larger molecules can be blocked.

In use a sample 90 comprising mobile ions, such as for example at least one of $Li^+$, $Na^+$, $K^+$, $Ca^{++}$, $Mg^{++}$, $Cl^-$ ions or the like may be placed in contact with ion access area 80 of the semiconductor device 10, such that mobile ions can diffuse into the gate insulation 60. For a typical transistor device, the diffusion of ions may be an undesired effect that may alter the transfer characteristics, i.e. the electrical properties of the transistor. The transfer characteristics relate to the electrical properties of the transistor device and may comprise a relation between a drain current $I_D$ and an applied gate source voltage $V_{GS}$. According to the techniques described herein, ion concentration of a sample may be determined based on measuring the modified transfer characteristics of transistor device 10 when ion access region 80 is brought in contact with a sample. According to these techniques, detection of such modified transfer characteristics may be used for determining the number of ions diffused into the gate insulation which in turn may indicate a measure for the ion concentration in the sample 90.

Figure 2:
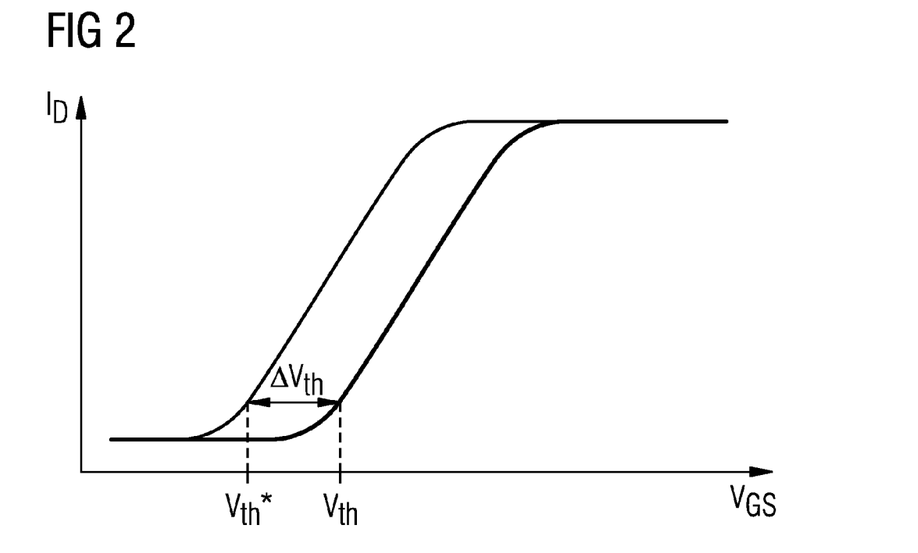
FIG. 2 shows the difference in the transfer characteristic of a field effect transistor structure depending on the ion concentration.

The transfer characteristic of the field effect transistor structure may be altered when ions are present in the gate insulation 60 as shown in FIG. 2. FIG. 2 shows one example of a modified transfer characteristic that may be measured and used as an indication of ion concentration within a sample. For example, FIG. 2 shows drain current $I_D$ of semiconductor device 10 vs. an applied gate-source potential $V_{GS}$ of semiconductor device 10. According to this example, the onset of an electric current flow between source and drain $I_{Don}$ may be defined by the so called threshold voltage $V_{th}$. $V_{th}$ may indicate the beginning of inversion, the accumulation of minority carriers at the Si faced side of the gate insulation/Si interface under the influence of a respective $V_{GS}$. $V_{th}$ may be in the range of 0.1 V to 3 V and may depend on the geometry and the design of the field effect transistor structure 10. The transfer characteristics may thereby represent a specific signature of a field effect transistor structure with certain properties and dimensions.

According to another example not depicted in FIG. 2, another transfer characteristic of a field effect transistor structure is the flat band voltage $V_{FB}$, which may indicate a point where the concentration of majority carriers in the bulk Si-substrate is equal to those in the vicinity of the gate insulation/Si interface.

When in contact with a sample, if mobile ions are present within the gate insulation 60 and are accumulated at the gate insulation/semiconductor interface 63, the transfer characteristics may be shifted away from the reference plot of transfer characteristics when semiconductor device 10 is not in contact with a sample. For example, as shown in FIG. 2, when placed in contact with a sample, the threshold voltage $V_{th}$ may be shifted from a reference plot towards higher or lower values of $V_{th}^*$. In addition, although not depicted in FIG. 2, and $V_{FB}$ may be shifted to $V_{FB}^*$, depending on the polarity of the ions. According to the example of FIG. 2, the shifted $\Delta V_{th}$ of the threshold voltage from $V_{th}$ to $V_{th}^*$ may be measured, and the measured $V_{th}^*$ may be used to indicate a presence and optionally a polarity of ions present within the sample. In some examples, the shifted $\Delta V_{th}$ can be quantified in mV value and may be defined by the quantity of mobile ions present at the gate insulation/semiconductor substrate interface 63 in the gate insulation 60, thus making $\Delta V_{th}$ an indicator for mobile ions present in the gate insulation 60. The resolution of mobile ion concentrations that can be detected with such a semiconductor sensor device may be defined by the resolution capability of shift in voltages $\Delta V_{th}$ or $\Delta V_{FB}$ of the device and may be in the Millivolts (mV) range, which may correspond to about 1E10 ions/cm². This may indicate a gate insulation/semiconductor interface with a mobile ion load of some ppm of a monolayer on the gate insulation faced side of the interface.

For the present disclosure, $I_D$ has the role of an auxiliary current only used for recording and determining the transfer characteristics. $I_D$ and the entire field effect transistor structure are not necessarily used for switching, amplification or other purposes. The present disclosure, however, may be combined or integrated in switching or other semiconducting devices.

Figure 3A:
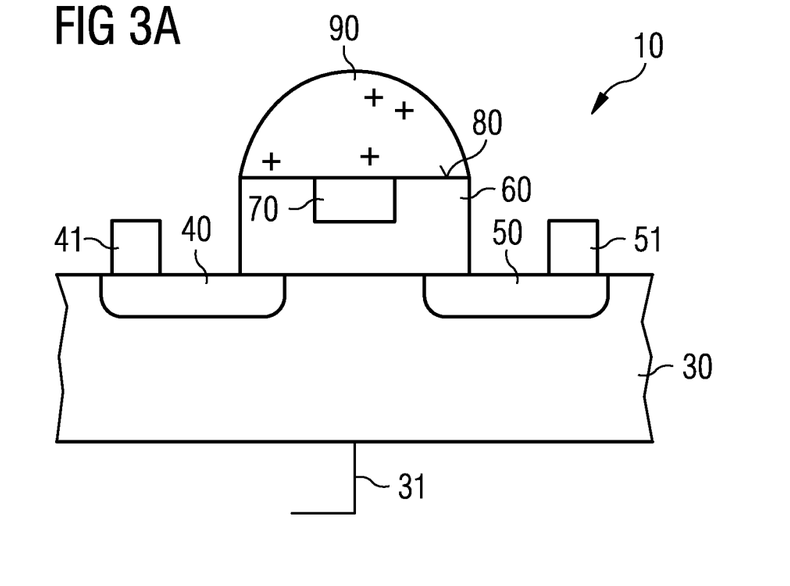
FIG. 3a to d shows how ions from a sample may be detected in a field effect transistor structure.

FIG. 3A to 3D are conceptual diagrams that illustrate generally in one example how ions in a sample may be determined. FIG. 3A illustrates a semiconductor device 10 with an access region 80 in contact with a droplet of a sample 90. In some examples, the sample 90 may be a liquid or a solid sample containing earth alkali ions such as $Li^+$, $Na^+$, $K^+$, $Ca^{++}$, $Mg^{++}$ or the like. These ions are mobile in the sample and may enter gate insulation 60 and are therefore referred to as mobile ions herein. As one example, the sample can be a liquid sample such as blood and the apparatus may be used for measuring the $K^+$ concentration in blood. The apparatus, however, can be equally used for negative ions such as $Cl^-$. The liquid sample may be, for example, water, drinking water, beverage, electrolytes or waste water, or any other type of liquid, and the semiconductor sensor can used for specifically determining an ion concentration in the sample.

The mentioned approach for measuring the quantity of mobile ions may be applied in medicinal routine measurements as e.g. $K^+$ in blood samples. This may enable the measurement of the K+ concentration in the blood sample, which may be described in mmol/l (millimole per liter of liquid sample). According to one specific example, a homogeneous K+ concentration in a blood sample may be ~4 mmol/l (i.e. ~10 ppm or ~1E18 ions/cm³). Detecting shifts in the transfer characteristics with devices (e.g., semiconductor device 10) based on field effect structures may enable detection of an amount of mobile ions at the gate oxide/Si interface down to about some 1E10 ions/cm² with an accuracy of some 10 mV for $\Delta V_{th}$.

Figure 3B:
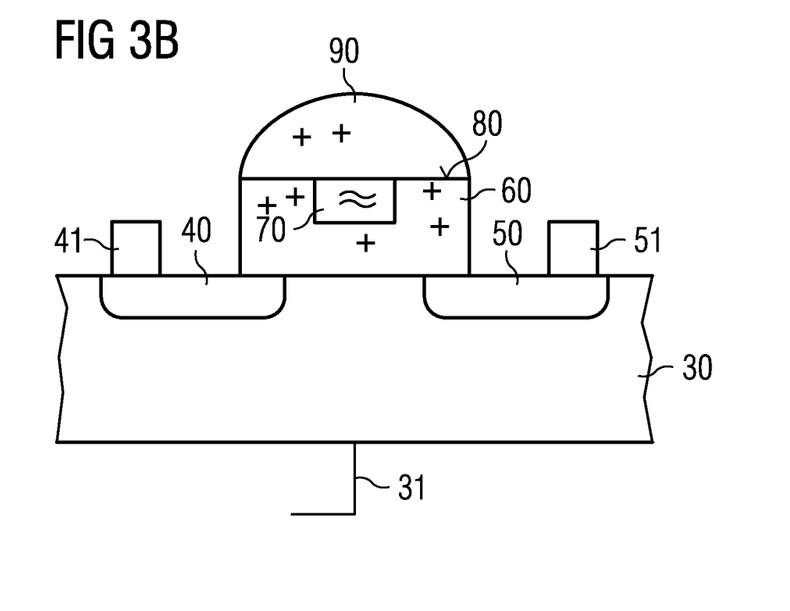

In many samples more than one type of ions may be present and separation of the different types of ions may be required. In order to be detected, mobile ions may be moved from a sample to the gate insulation 60 (FIG. 3B). The sample may be placed substantially in contact with the ion access area 80 as illustrated for the field effect transistor structure 10 of FIG. 1 in FIG. 3A.

Figure 3C:
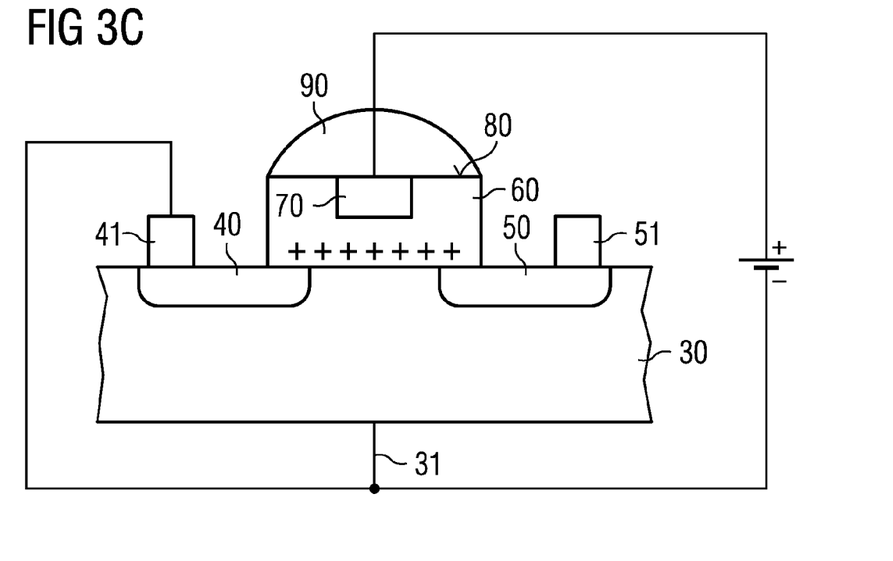

Furthermore, the mobile ions may move from the sample 90 into the gate insulation 60 and in particular to the gate insulation/semiconductor body interface 63 (FIGS. 3B and 3C).

The transport of the mobile ions in insulating materials such as the gate insulation may be thermodynamically enabled by means of driving forces as gradients in the chemical potential (diffusion) or electric fields (drift). Drift, diffusion, or both can be used to transport the mobile ions from the sample into the gate insulation for quantification as illustrated in FIGS. 3B and 3C.

(a) Diffusion. Caused by chemical gradients, there is the tendency of mobile ions to have a homogonous distribution throughout the gate insulation. This transport can be described by Fick's second law of diffusion, with existing analytical solutions for the situation of having a defined mobile ions source at the interface between the mobile ion containing sample and the gate insulation. Kinetics of diffusion varies with the species of mobile ion, generally related to their respective ionic radii. Thus, smaller ions diffuse much faster through the separation layer. Diffusion can therefore be enhanced by increasing the temperature in the gate insulation. The gate electrode can be designed to be heatable for increasing the temperature of the gate electrode 70, and in turn the adjacent gate insulation 60. Polycrystalline silicon can be used for the heatable gate electrode.

(b) Drift: Differences of electric potentials on opposing sites of the gate insulation may cause an electric field, which may act as a driving force for mobile ion drift. Coupled with diffusion phenomena, there may be a tendency to reach the electrochemical equilibrium. However, generally the drift dominates significantly diffusion, which may cause mobile ions to be transported towards the side of the gate insulation that exhibit lower electric potential, which may thereby represent the cathode of the system. The electric drift can generally be described by Ohm's law. Treating the gate insulation as a resistor against mobile ion transport, the applied voltage may result in a certain flux of mobile ions towards the cathode. If a gate-source and/or a gate-bulk potential $V_{GS}$ (bulk and source may be on the same electrical potential) is applied to the field effect transistor structure, an electrical field may be generated over the gate insulation 60 comparable to a plate capacitor and ions that are mobile in the gate insulation drift in the gate insulation and drift will be the dominating factor compared to diffusion.

Figure 3D:
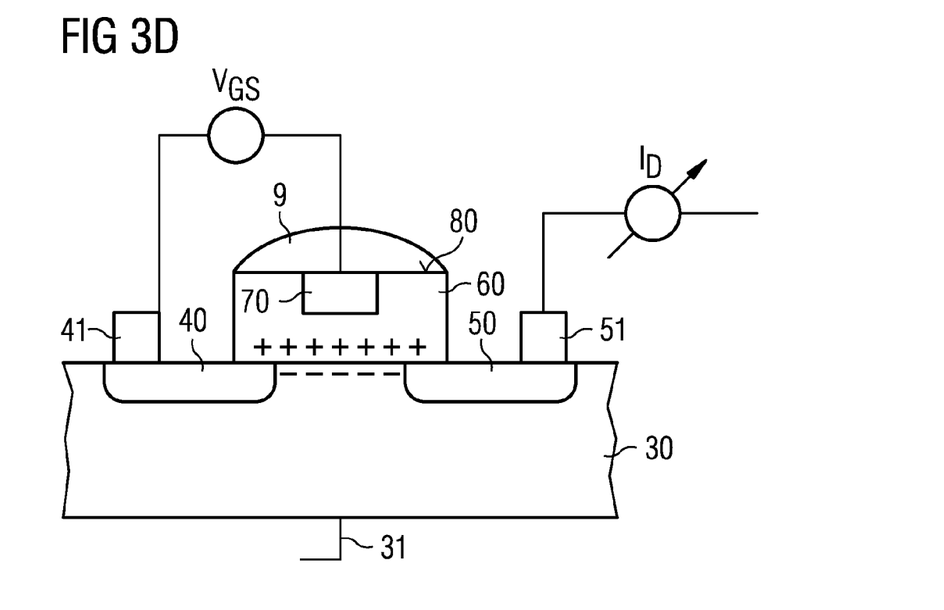

Using a combination of diffusion and drift in process termed bias-temperature stress, for example a combination of heating the gate electrode 70 (FIG. 3B) and applying and adjusting a voltage between the gate electrode 70 and the source region 40 and/or the bulk or body region 30 (FIG. 3C), mobile ions of different size and charge will move at different velocities. In this way, different species of mobile ions, such as $Li^+$, $Na^+$, $K^+$, $Ca^{++}$, $Mg^{++}$ and other ions can be separated such that only one ion species may be transported to the gate insulation 60/bulk semiconductor interface (FIG. 3C) and only this species is detected, when $V_{th}$, $V_{th}^*$, and/or $\Delta V_{th}$ is determined (FIG. 3D)

Figure 4:
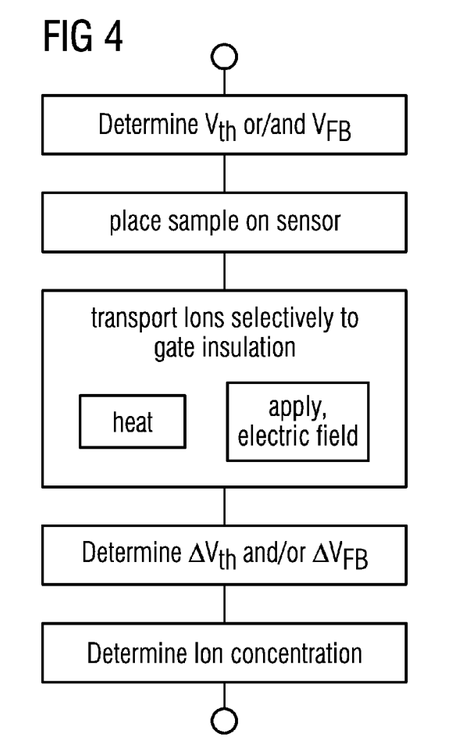
FIG. 4 shows a flow chart of how ions from a sample may be detected in a field effect transistor structure.

A flow chart of an example of a measurement process is illustrated in FIG. 4.

Figure 5:
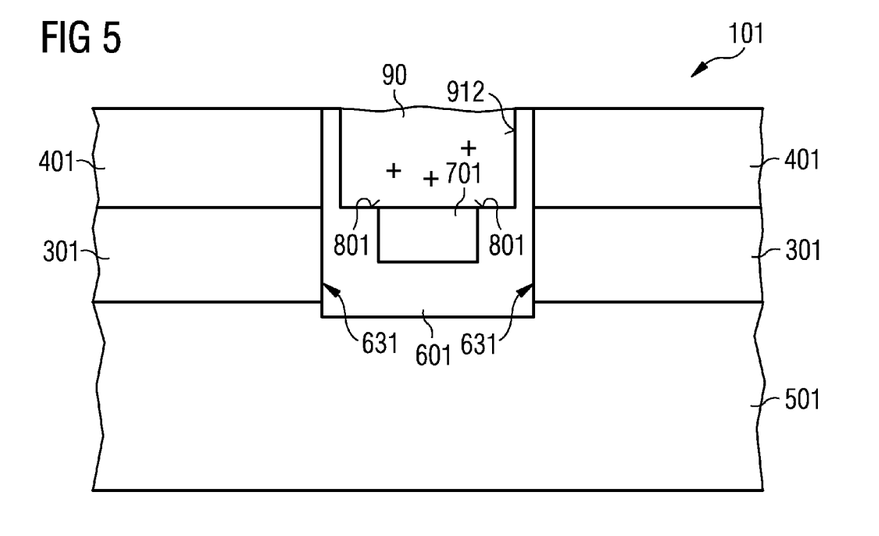
FIG. 5 shows an example of a vertical field effect transistor structure for detection ions in a sample.
Figure 6:
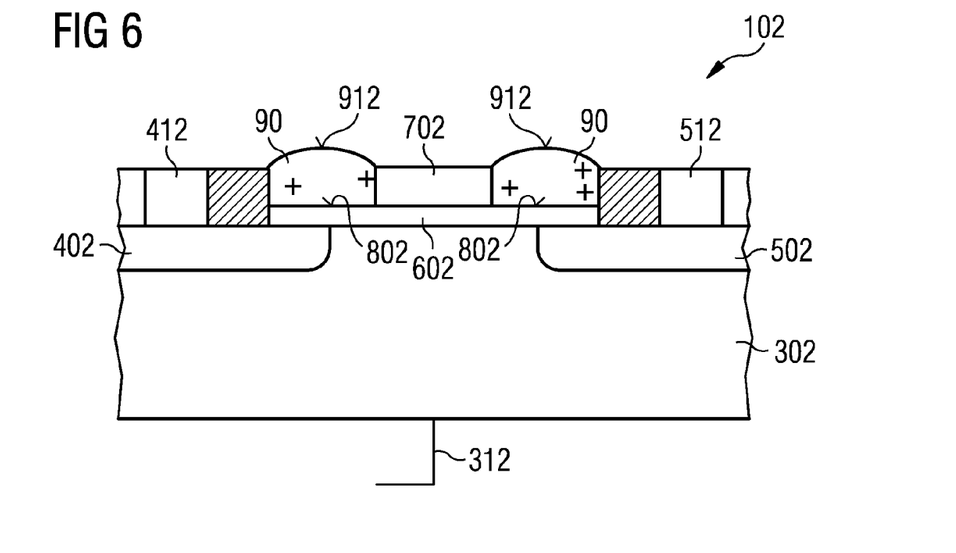
FIG. 6 shows an example of a lateral field effect transistor structure for detection ions in a sample.
Figure 7:
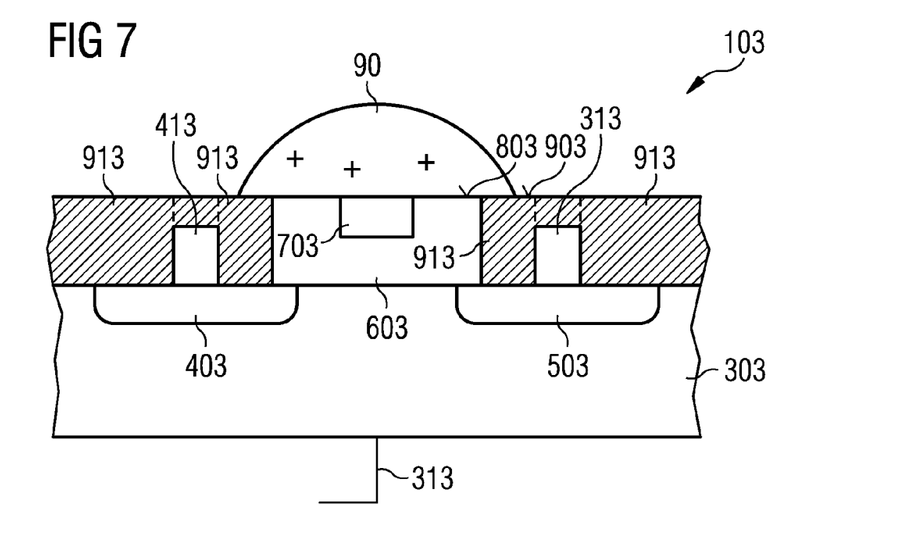
FIG. 7 shows an example of a further lateral field effect transistor structure for detection ions in a sample.

While FIG. 1 shows one possible field effect transistor structure for detecting ions in a sample, FIGS. 5, 6, and 7 show additional examples of field effect transistor structures that may also be used for detecting ions in a sample. Further modification of combinations of features shown in one example may be combined with other examples. The methods described above with respect to FIGS. 1 and 3 can be equally applied to the field effect transistor structures shown in FIGS. 5, 6, and 7.

FIG. 5 shows a vertical field effect transistor structure 101 in which the gate insulation 601 and the gate electrode 701 are arranged in a trench. A body region 301 is arranged between the source region 401 and the drain region 501. For example, the body region may be p-type and the drain region 501 and the source region may be n-type.

According to the example of FIG. 5, the gate electrode 701 is arranged inside the trench in the same vertical position as the body region 301. A sample cavity 912 remains above the gate electrode 701 into which the sample liquid 90 can be added. The cavity provides a defined volume for the sample.

As shown in the example of FIG. 5, the sensor principle of the present disclosure may be used with vertical semiconductor structures.

FIG. 6 shows a further example of a lateral field effect transistor structure 102 providing cavities 912 into which the liquid sample 90 can be filled. According to the example of FIG. 6, the gate insulation 602 is arranged at the bottom of the cavities 912 and a gate electrode 702 is arranged at some place on the gate insulation 602. A source region 402 with source contact 412, a bulk region 302 with a bulk contact 312, and a drain region 502 with drain contact 512 may be arranged as described with respect to FIG. 1.

FIG. 7 shows a further example of a lateral field effect transistor structure 103 providing a substantially flat surface 903 onto which the sample 90 can be placed. According to the example of FIG. 7, no cavity may be filled which might be helpful with larger sample volumes or liquid sample having a high surface tension. According to the example of FIG. 7, a portion of the planar or flat surface 903 is provided by the gate insulation 603 forming the ion access area 803. The gate insulation 603 may be bowl shaped or U-shaped and may be filled by a gate electrode 703. A protective filling material 913 may be used to provide a substantially planar surface around the ion access area 803 of the gate insulation 603.

A source region 403 with source contact 413, a bulk region 303 with a bulk contact 313, and a drain region 503 with drain contact 513 may be arranged similar to the examples described with respect to FIG. 1 or 6.

The examples shown and described with respect to the figures relate to field effect transistor structures, i.e. semiconductor structures that have the main features and elements of the FET. They may not, in some examples, be directly used as transistors and their transistor functions may be limited. The transistors described herein are therefore termed field effect transistor structures. While the examples have been described herein with respect to different field effect transistor structures (FET and MOSFET structures), the invention may also be applied with other field effect or gated semiconductor devices such as for example IGBTs or gated diodes.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. It is intended that this invention is limited only by the claims and the equivalents thereof.

The invention claimed is:

1. An apparatus for determining an ion concentration in a sample, comprising:
   a semiconductor body;
   a gate electrode;
   a gate insulation arranged between the gate electrode and at least a portion of the semiconductor body, wherein the gate insulation comprises at least one ion access area providing access for ions in the sample to the insulating layer, wherein the gate electrode is in direct contact with the gate insulation, wherein the gate electrode is embedded in the gate insulation so that a top surface of the gate electrode and a top surface of the gate insulation are coplanar.

2. The apparatus of claim 1, further comprising a detection module to detect a change in at least one electrical property of the semiconductor device to determine an ion concentration of the sample.

3. The apparatus of claim 1, wherein the gate insulation is a gate oxide made from silicon oxide.

4. The apparatus of claim 1, wherein the semiconductor body is made from silicon.

5. The apparatus of claim 1, wherein the semiconductor body comprises at least one p-conducting area, at least one n-conducting area, and at least one p-n-junction between the at least one p-conducting area and the at least one n-conducting area.

6. The apparatus of claim 1, wherein the gate electrode is made from polycrystalline silicon.

7. The apparatus of claim 1, wherein the gate electrode is heatable.

8. The apparatus of claim 1, wherein the at least one ion access area comprises an ion permeable surface.

9. The apparatus of claim 1, wherein the at least one ion access area is an area where the insulating layer is in use in contact with the sample.

10. The apparatus of claim 1, wherein the apparatus comprises a sample cavity for receiving the sample and wherein the at least one ion access area is arranged in the sample cavity.

11. The apparatus of claim 1, wherein the apparatus has the structure of a field effect transistor and the semiconductor body comprises the source area of a first conductivity type, the drain area of the first conductivity type and a body area of a second conductivity type opposite to the first conductivity type between the source area and the drain area, and wherein the gate insulation is arranged between the gate electrode and at least the body area.

12. The apparatus of claim 1, wherein the semiconductor body comprises a source region, a drain region and a body region arranged between the source region and the drain region, and wherein the gate electrode terminates laterally before extending over the source region and the drain region.

13. A method for determining an ion concentration in a sample, the method comprising:
providing a sample in contact with an ion access area of a gate insulation of a semiconductor field effect device structure;
transporting ions from the sample into the gate insulation;
determining a change in an electric characteristic of the field effect device structure due to transportation of the ions from the sample into the gate insulation of the semiconductor field effect device structure; and
determining the ion concentration within the sample based on the change in the electric characteristic of the semiconductor field effect device structure.

14. The method of claim 13, further comprising: heating a gate electrode or the gate insulation to increase transportation of the ions from the sample into the gate insulation.

15. The method of claim 13, further comprising: applying an electric field to the gate insulation to increase transportation of the ions from the sample into the gate insulation.

16. The method of claim 13, wherein transporting ions from the sample into the gate insulation comprises selectively transporting at least one predetermined type of ions.

* * * * *